United States Patent [19]

Caldwell

[11] Patent Number: 5,183,829
[45] Date of Patent: Feb. 2, 1993

[54] ORAL LIQUID COMPOSITIONS OF NON-STEROIDAL ANTI-INFLAMMATORY DRUGS

[75] Inventor: Henry C. Caldwell, Ambler, Pa.

[73] Assignee: Applied Analytical Industries, Inc., Wilmington, N.C.

[21] Appl. No.: 766,774

[22] Filed: Sep. 27, 1991

[51] Int. Cl.$^5$ ...................... A61K 31/19; A61K 31/40
[52] U.S. Cl. ...................................... 514/570; 514/420
[58] Field of Search .................................. 514/570, 420

[56] References Cited

U.S. PATENT DOCUMENTS 4,704,405 11/1987 O'Neill et al. ...................... 514/568
4,880,835 11/1989 Park ...................................... 514/570

FOREIGN PATENT DOCUMENTS 2059768 4/1961 United Kingdom .

OTHER PUBLICATIONS

Najib, Int. Jour. Pharmaceutics, 45, p. 139 (1988).
Chan et al., Pharm. Research 7 1027 (1990).

Primary Examiner—S. J. Friedman
Attorney, Agent, or Firm—William H. Edgerton

[57] ABSTRACT

Pharmaceutically elegant oral compositions of non-steroidal anti-inflammatory drugs or their salts are prepared by adding selected dispersing agents such as a polyvinylpyrrolidone, hydroxypropyl-methylcellulose or hydroxypropylcellulose to the NSAIDs in a medium of polyol-glycol-alcohol. The compositions offer the formation of finely dispersed active ingredients upon dispersion in gastric juice.

12 Claims, No Drawings

ORAL LIQUID COMPOSITIONS OF NON-STEROIDAL ANTI-INFLAMMATORY DRUGS

This invention relates to improved one-phase liquid compositions of non-steroidal anti-inflammatory agents for oral administration.

BACKGROUND OF THE INVENTION

U.S. Pat. No. 4,880,835 describes the preparation of oral liquid compositions of calcium sulindac using a pharmaceutical vehicle comprised of a glycol, a polyol and an optional alcohol. That patent describes the problems of absorption of drug from the gut which are present in the art.

K. Chan et al., Pharm. Research, 7 1027 (1990) demonstrated that sodium diclofenac was more bioavailable orally from an enteric coated tablet than from an aqueous solution. This is contrary to the expectation of the art and confirms the fact that a problem exists in the art. U.S. Pat. No. 4,704,405 also describes the problem of absorption of NSAID's from the gastrointestinal track, especially as applied to sulindac.

N. M. Najib et al., International Journal of Pharmaceutics, 45 139 (1988) has reported that ibuprofen-polyvinylpyrrolidone in contact may form a weak acid-weak base type of complex in the solid state or in solution. This reference does not report any studies in the glycol-polyol media of the present invention. Nor does there exist any suggestion in Najeb that a pharmaceutically elegant preparation of NSAID's which has exceptional behavior upon dispersion in gastric juice is formed by the use of certain selected dispersing agents.

U.K. Patent No. 2,059,768 describes the formation of more soluble derivatives of NSAID's with the TRIS group of compounds.

I have now confirmed that the oral liquid compositions of NSAID's which are described in U.S. Pat. No. 4,880,835, at best, equal the release of drug from ingestion of the solid pharmaceutical form on the market. Further, I have discovered that when NSAID's contained in liquid carriers contact acid gastric fluid, the drug forms a sticky agglomerate which separates from the acid supernatant liquid. The active NSAID agent, therefore, becomes available for absorption only by being broken up during mechanic agitation, an uncertain and unreliable method of delivery.

SUMMARY OF THE INVENTION

This invention relates to improved oral liquid compositions of non-steroidal anti-inflammatory drugs which demonstrate good reproducible distribution in gastric juice and, thereby, better absorption of active ingredient into the subject. The compositions contain one or more NSAID's dissolved in a glycol-polyol-alcohol vehicle along with one or more selected dispersing agents, especially polyvinylpyrrolidone of a certain viscosity range.

DETAILED DESCRIPTION OF THE INVENTION

This invention is based on the discovery that selected dispersing agents which are known and used in the drug and food industries are able to disperse non-steroidal anti-inflammatory drugs in the stomach when added to certain oral liquid compositions of the NSAID's prior to ingestion. The compositions also maintain their good pharmaceutical properties prior to ingestion.

Further, the discovery is based on demonstrations that NSAID's which have acid groups in their chemical structures, when formulated into pharmaceutically elegant liquid compositions form sticky, often highly colored agglomerates upon dumping into gastric juice. A testing system which is based on optical density and which is similar to one accepted by the U.S.P. has been devised to ascertain the degree of dispersion of the active NSAID composition upon dumping into gastric fluid (SGF). Many standard dispersing or suspending agents of the art have no beneficial effect on the biological efficacy of the NSAID-vehicle compositions which are described in U.S. Pat. No. 4,880,835.

The improved oral liquid compositions of this invention comprise from 0.5-7%, preferably 1-5%, w/v, of NSAID; 15-50%, preferably 20-40%, v/v of a glycol such as propylene glycol or polyethyleneglycol; 0-20% v/v of ethanol; from 30-80%, preferably 35-75%, v/v of a polyol such as sorbitol or glycerin; and from 50:1 to 1:3, w/w ratio of NSAID: polymer, of a pharmaceutically acceptable dispersing agent selected from the group consisting of polyvinylpyrrolidone (PVP), hydroxylpropylcellulose (HPC) and hydroxypropylmethylcellulose (HPMC).

The preferred dispersing agent is PVP K-25-32. The numbers relate to the molecular weight of the polymer. For example, PVP K-30 has an average molecular weight of about 40,000 with attendant viscosity characteristics. Dispersing polymers must be selected so not to make the final liquid composition too viscous but which also offer a clear, pharmaceutically elegant appearance. Hydroxypropyl-methylcellulose E and hydroxypropylcellulose EF were the preferred dispersing agents in the cellulose groups.

Other pharmaceutical additives may be mixed with those described above, for example, sweetening agents, local anesthetics, anti-bacterials and the like. Also the glycol or polyol ingredients may be mixed, such as using a sorbitol-glycerin mixture as a component of the vehicle.

The optimal ratios of NSAID to dispersing agents are 1:30 w/w (NSAID: polymer) for polyvinylpyrrolidone K-28-30; and 1:1 for hydroxypropylmethylcellulose E-5 and 1:1 for hydroxypropylcellulose EF.

One skilled in the art will recognize that the critical function of the dispersing agent in the liquid oral compositions of this invention must depend on several factors. First it must offer a final product which is clear, stable, pleasing to the eye and taste as well as not too viscous. Second, it must be able to offer a proper dispersion of the active agent when introduced into a strongly acid, aqueous medium such as gastric juice. It must not yield an agglomerate or a flocculant material upon dilution but, rather, a fine dispersion of biologically active ingredient.

The active ingredient in the improved oral liquid compositions of this invention is selected from the family of well-known non-steroidal drugs which have anti-inflammatory analgesic activity (NSAID's) and which have a functional carboxylic acid group in their chemical structures. Particularly included are the non-toxic, pharmaceutically acceptable alkali metal or ammonium salts of said acids which are prepared as described in the literature. Exemplary are the sodium, potassium, tromethamine or, especially, calcium salts. In fact, the salts are usually preferred over the free acid forms because of their ease of handling. Also included are the optical isomers of said NSAID's such as S(+) ibuprofen.

The NSAID's are those acceptable for administration to humans. Many are described, along with their approved dosage regimens, in the *Physician's Desk Reference*, the *Merck Index* or similar references. The suitability of the NSAID for the described compositions can be ascertained by adding a prescribed quantity to U.S.P. simulated gastric fluid (SGF). If the acid form of the NSAID tends to agglomerate in the container, a problem of absorption of active agent from the gut may well be present. The use of the improved pharmaceutical vehicle described herein usually gives a fine suspension or dispersion to the eye upon dispersal.

The NSAID active ingredients to be used in this invention are exemplified by the following groups:

A. The aralkylcarboxylic acids such as diclofenac, fenoprofen, flurbiprofen, ibuprofen, indomethacin, ketoprofen, ketoralac, naproxen, sulindac, etodolac, tolmetin; and B. The arylcarboxylic acids such as diflunisal, mefenamic acid, meclofenamic acid, flufenamic acid.

The improved pharmaceutical compositions of this invention are prepared by mixing the constituents, filtering the mix and filling into bottles of appropriate size.

The glycol and polyol constituents of this invention are those acceptable for internal pharmaceutical purposes. The glycol may be propylene glycol or one of the polyalkylene glycol products such as those known in the art as the "PEG" series with chemical structures having 2 or 3 carbon atoms in the alkylene moiety of their chemical structures and a mean molecular weight of 200 to 4000. The polyol constituent comprises pharmaceutically acceptable solvent products having more than two hydroxyls in their chemical structures such as glycerin or sorbitol.

The oral compositions are usually formulated to deliver about 50–250 mg of drug per teaspoon of a pleasant tasting liquid product which will have enhanced activity. The preferred NSAID's are sulindac, diclofenac, ketoprofen, naproxen and ibuprofen.

The following analytical procedures were used to ascertain the method of behavior of the carboxylic acid forms of NSAID's upon contact with acid media:

A. Dissolution

The USP XXII (p. 1,304) sulindac tablet dissolution method was used; pH 7.2 phosphate buffer, apparatus 2 at 50 rpm, pull times were 10, 20, 30, 45 minutes. At 45 minutes, the speed was increased to 250 rpm and a 60 minutes infinity sample was pulled. Samples were assayed by ultraviolet light at 326 nm.

B. Homogeneity by assay

The above-mentioned procedure was used, but simulated gastric fluid (SGF) USP (without enzymes) was the vehicle. Samples were pulled at 10, 20, 30, 40, 50 and 60 minutes, diluted with an equal volume of methanol and assayed by ultraviolet light at 326 nm.

C. Dispersion

The procedure was as above with SGF, but samples were pumped to the ultraviolet cell and read at 530 nm every 5 minutes. The cells and hoses were rinsed with methanol and SGF between readings.

The operators observed that usually the free acid form of the NSAID tended to adhere to the paddle and rod of the apparatus in the form of a sticky agglomerate. The higher the conductance of the light through the charged apparatus, the greater the removal of active drug from the solution to form agglomerate. The lower the conductance, the more the drug has formed a clouding dispersion of particles. Details of the results of the testing program are reproduced in the examples since they are critical to this invention.

The following embodiments of the invention are designed to illustrate and teach the specific use of the invention but not to limit its scope.

EXAMPLE 1

General Directions for Preparation

1. Mix ethanol, water and propylene glycol in a container.
2. Add NSAID, calcium hydroxide and calcium saccharin then mix with gentle heating until all the particles are dissolved.
3. Add polyvinylpyrrolidone (PVP 28-30) and dissolve.
4. Add menthol and dissolve.
5. Add sorbitol solution or glycerin to make up the volume.
6. Filter through a clarifying filter and fill.

The preparation is administered orally, in the amount of from 1-6 teaspoons per day, each containing a non-toxic, anti-inflammatory quantity of NSAID, to a patient in need of anti-inflammatory and/or analgesic treatment.

EXAMPLE 2

Preparation of Sulindac Liquid Preparations

The following liquid compositions were prepared as described above using v/v or w/v quantities depending on the physical state of the ingredient.

| Formulation Ingredients | A % | B % | C % | D % | E % |
|---|---|---|---|---|---|
| Ethyl alcohol | 10.0 | 10.0 | 10.0 | 10.0 | 10.0 |
| Propylene glycol | 25.0 | 25.0 | 25.0 | 25.0 | 25.0 |
| Water | 5.0 | 5.0 | 5.0 | 5.0 | 5.0 |
| Sulindac | 4.0 | 4.0 | 4.0 | 4.0 | 4.0 |
| Calcium hydroxide | 0.415 | 0.415 | 0.415 | — | — |
| Calcium saccharin | 0.3 | 0.3 | 0.3 | 0.3 | 0.3 |
| PVP C-30 | 4.0 | — | 4.0 | — | — |
| L-Menthol | — | 0.2 | 0.2 | 0.2 | 0.2 |
| Sodium hydroxide | — | — | — | 0.45 | 0.45 |
| PVP K 28-32 | — | — | — | 4.0 | — |
| Sorbitol/Glycerin (9:1) | Q.S. | Q.S. | Q.S. | Q.S. | Q.S. |
| | 100.0 | 100.0 | 100.0 | 100.0 | 100.0 |

EXAMPLE 3

Calcium Sulindac Liquid and Tablet Dissolution

| | Formulations | | |
|---|---|---|---|
| Time (Minutes) | A | B | Commercial Tablet (200 mg) |
|---|---|---|---|
| 10 | 101.0 | 83.2 | 87.5 |
| 20 | 100.5 | 89.1 | 91.1 |
| 30 | 100.1 | 91.0 | 91.8 |
| 45 | 100.3 | 91.5 | 93.1 |
| 60 | 100.3 | 96.9 | 98.2 |

The letter designations herein and hereafter refer to the compositions described in Example 2. The results are the percent dissolved.

EXAMPLE 4

| | Sulindac (%) SGF at Mid-Point of Flask | |
|---|---|---|
| Time | Formulations | |
| (Minutes) | C | B |
| 10 | 97.6 | 76.2 |
| 20 | 97.1 | 70.2 |
| 30 | 93.4 | 70.3 |
| 40 | 94.0 | 61.3 |
| 50 | 91.6 | 60.1 |
| 60 | 90.9 | 62.7 |

EXAMPLE 5

| | Light Transmission (%) of 5 ml and 2.5 ml of 200 mg/5 ml Calcium Sulindac Liquid in SGF | | | |
|---|---|---|---|---|
| Time | Formulations | | | |
| (Minutes) | C(5) | B(5) | C(2.5) | B(2.5) |
| 5 | 0.88 | 4.35 | 23.6 | 26.8 |
| 10 | 0.85 | 10.92 | 21.3 | 32.3 |
| 15 | 0.85 | 18.43 | 20.7 | 36.9 |
| 20 | 0.93 | 26.21 | 20.8 | 41.9 |
| 25 | 1.0 | 35.22 | 21.1 | 46.6 |
| 30 | 1.08 | 42.11 | 21.4 | 51.6 |
| 35 | 1.15 | 51.00 | 21.7 | 56.6 |
| 40 | 1.25 | 56.98 | 22.5 | 62.9 |
| 45 | 1.31 | 67.03 | 23.3 | 70.1 |
| 50 | 1.43 | 71.39 | 23.8 | 73.6 |
| 55 | 1.53 | 77.39 | 24.4 | 76.4 |
| 60 | 1.66 | 87.29 | 25.4 | 80.1 |

EXAMPLE 6

| | Sodium Sulindac % Transmission in SGF | |
|---|---|---|
| Time | Formulations | |
| (Minutes) | PVP | NO PVP |
| 5 | 1.4 | 4.3 |
| 10 | 1.1 | 9.8 |
| 15 | 1.1 | 16.7 |
| 20 | 1.2 | 23.4 |
| 25 | 1.2 | 30.0 |
| 30 | 1.3 | 35.9 |
| 35 | 1.3 | 41.7 |
| 40 | 1.5 | 47.2 |
| 45 | 1.5 | 52.5 |
| 50 | 1.7 | 59.8 |
| 55 | 1.7 | 67.5 |
| 50 | 1.9 | 75.3 |

EXAMPLE 7

| Ibuprofen Composition and Properties | | | |
|---|---|---|---|
| Formulations | A | B | C |
| Ingredients | % | % | % |
| Ethyl alcohol | 10.0 | 10.0 | 10.0 |
| Propylene glycol | 25.0 | 25.0 | 25.0 |
| Water | 5.0 | 5.0 | 5.0 |
| Ibuprofen | 4.0 | 4.0 | 4.0 |
| Calcium hydroxide | 0.72 | 0.72 | 0.72 |
| Calcium saccharin | 0.3 | 0.3 | 0.3 |
| PVP K 28-32 | 4.0 | 4.0 | — |
| Sucrose | — | 10.0 | — |
| Sorbitol/Glycerin (9:1) | Q.S. | Q.S. | Q.S. |
| | 100.0 | 100.0 | 100.0 |

| | Light Transmission (%) of 200 mg/5 ml of the Above Calcium Ibuprofen Liquids in SGF | |
|---|---|---|
| Time | Formulations | |
| (Minutes) | A | C |
| 5 | 40.7 | 96.5 |
| 10 | 38.1 | 96.8 |
| 15 | 36.7 | 96.7 |
| 20 | 35.7 | 97.6 |
| 25 | 35.3 | 97.6 |
| 30 | 35.3 | 97.5 |
| 35 | 35.2 | 97.9 |
| 40 | 35.3 | 98.1 |
| 45 | 35.4 | 98.9 |
| 50 | 35.3 | 97.8 |
| 55 | 35.1 | 98.0 |
| 60 | 34.9 | 98.1 |

EXAMPLE 8

| Fenoprofen Composition and Properties | | |
|---|---|---|
| Formulations | A | B |
| Ingredients | % | % |
| Ethyl alcohol | 10.0 | 10.0 |
| Propylene glycol | 25.0 | 25.0 |
| Water | 5.0 | 5.0 |
| PVP K -28-32 | 4.0 | — |
| Fenoprofen calcium | 4.61 | 4.61 |
| Calcium saccharin | 0.3 | 0.3 |
| Sorbitol/Glycerin (9:1) | Q.S. | Q.S |
| | 100.0 | 100.0 |

| | Light Transmission (%) of 200 mg/5 ml of Calcium Fenoprofen Liquid in SGF | |
|---|---|---|
| Time | Formulations | |
| (Minutes) | A (5 ml) | B (5 ml) |
| 5 | 39.5 | 95.6 |
| 10 | 33.7 | 94.8 |
| 15 | 30.5 | 94.7 |
| 20 | 28.4 | 94.6 |
| 25 | 26.6 | 93.8 |
| 30 | 25.2 | 92.9 |
| 35 | 24.6 | 93.2 |
| 40 | 23.6 | 92.9 |
| 45 | 23.2 | 92.7 |
| 50 | 22.3 | 92.2 |
| 55 | 21.8 | 92.5 |
| 60 | 21.6 | 92.7 |

EXAMPLE 9

| Ketoprofen Compositions and Properties | | |
|---|---|---|
| Formulations | A | B |
| Ingredients | % | % |
| Ethyl alcohol | 10.0 | 10.0 |
| Propylene glycol | 25.0 | 25.0 |
| Water | 5.0 | 5.0 |
| Ketoprofen | 1.5 | 1.5 |
| Tris (Tromethamine) | 0.71 | 0.71 |
| Calcium saccharin | 0.3 | 0.3 |
| PVP K 28-32 | — | 1.5 |
| Sorbitol/Glycerin (9:1) | Q.S. | Q.S. |
| | 100.0 | 100.0 |

Light Transmission (%) of 75 mg/5 ml of TRIS Ketoprofen in SGF

| Time (Minutes) | Formulations B (25 ml) | A (25 ml) |
|---|---|---|
| 5 | 66.9 | 97.1 |
| 10 | 62.9 | 97.2 |
| 15 | 60.8 | 96.9 |
| 20 | 60.4 | 96.3 |
| 25 | 59.6 | 96.7 |
| 30 | 61.0 | 96.2 |
| 35 | 60.3 | 96.0 |
| 40 | 60.1 | 96.2 |
| 45 | 60.4 | 95.9 |
| 50 | 60.0 | 95.6 |
| 55 | 59.5 | 96.1 |
| 60 | 61.3 | 96.0 |

EXAMPLE 10

Naproxen Compositions and Properties

| Formulations Ingredients | A % | B % |
|---|---|---|
| Ethyl alcohol | 10.0 | 10.0 |
| Propylene glycol | 25.0 | 25.0 |
| Water | 5.0 | 5.0 |
| Naproxen | 2.5 | 2.5 |
| TRIS | 1.32 | 1.32 |
| Calcium saccharin | 0.3 | 0.3 |
| L-Menthol | 0.2 | 0.2 |
| PVP K 28-32 | — | 1.5 |
| Sorbitol/Glycerin (9:1) | Q.S. | Q.S. |
| | 100.0 | 100.0 |

Percent Light Transmission In 1 cm. Cell of 20 ml Of TRIS Naproxen

Solution With Varying Amounts Of Polyvinylpyrrolidone (PVP 28-30) In 900 ml USP SGF (no enzyme) Stirred At 50 r.p.m.

| Time | Formulations A | B | C | D | E |
|---|---|---|---|---|---|
| 5 | 3.4 | 13.0 | 39.7 | 25.7 | 39.8 |
| 10 | 14.3 | 12.6 | 39.2 | 33.6 | 42.4 |
| 15 | 12.9 | 12.9 | 37.6 | 29.4 | 41.8 |
| 20 | 12.2 | 10.6 | 33.9 | 28.2 | 47.0 |
| 25 | 13.4 | 11.1 | 38.2 | 26.2 | 30.0 |
| 30 | 12.9 | 11.2 | 36.3 | 24.8 | 33.6 |
| 35 | 10.7 | 13.1 | 34.8 | 30.2 | 45.7 |
| 40 | 11.9 | 9.7 | 33.3 | 29.0 | 50.8 |
| 45 | 14.9 | 12.2 | 34.0 | 26.4 | 42.8 |
| 50 | 14.0 | 10.8 | 34.8 | 25.4 | 41.9 |
| 55 | 13.4 | 11.8 | 34.2 | 23.6 | 36.8 |
| 60 | 14.5 | 11.1 | 34.4 | 26.8 | 39.8 |

A Naproxen:PVP 1:1
B Naproxen:PVP 10:1
C Naproxen:PVP 100:1
D Naproxen:PVP 50:1
E Vehicle Without Naproxen.

EXAMPLE 11

HPC: Sulindac Compositions and Properties

The composition of Example 1, Sample B with hydroxypropylcellulose (EF) at ratios of 10:1, 50:1 and 100:1 w/w were compared with Sample B as control.

| Time | 10:1 | 50:1 | 100:1 | B |
|---|---|---|---|---|
| 5 | 1.2 | 1.7 | 2.4 | 3.4 |
| 10 | 1.2 | 3.0 | 5.1 | 8.9 |
| 15 | 1.3 | 5.2 | 9.6 | 15.7 |
| 20 | 1.4 | 8.2 | 14.5 | 23.1 |
| 25 | 1.5 | 12.3 | 19.4 | 29.6 |
| 30 | 1.6 | 14.6 | 24.8 | 37.0 |
| 35 | 1.7 | 20.8 | 30.8 | 42.8 |
| 40 | 1.8 | 33.6 | 38.4 | 48.5 |
| 45 | 1.8 | 52.8 | 46.8 | 55.3 |
| 50 | 1.9 | 85.1 | 56.7 | 61.4 |
| 55 | 2.0 | 78.1 | 73.8 | 68.9 |
| 60 | 2.2 | 84.3 | 87.8 | 79.6 |

EXAMPLE 12

HPMC: Sulindac Compositions and Properties

The composition of Example 1 Sample B with hydroxypropylmethylcellulose (E) at ratios of 10:1, 50:1 and 100:1 were compared with control Sample B as control.

| Time | 10:1 | 50:1 | 100:1 | B |
|---|---|---|---|---|
| 5 | .9 | 2.2 | 2.3 | 3.4 |
| 10 | 1.0 | 4.1 | 5.1 | 8.9 |
| 15 | 1.2 | 6.6 | 9.2 | 15.7 |
| 20 | 1.2 | 9.4 | 14.0 | 23.1 |
| 25 | 1.3 | 12.2 | 18.8 | 29.6 |
| 30 | 1.4 | 14.7 | 24.2 | 37.0 |
| 35 | 1.5 | 17.3 | 30.1 | 42.5 |
| 40 | 1.6 | 19.6 | 36.5 | 48.5 |
| 45 | 1.7 | 21.8 | 46.3 | 55.3 |
| 50 | 1.9 | 24.1 | 52.2 | 61.4 |
| 55 | 1.9 | 26.7 | 68.5 | 68.9 |
| 60 | 2.1 | 29.5 | 82.8 | 79.6 |

Other dispersing agents known to the art were unsatisfactory either because (1) they did not form acceptable liquid compositions of the NSAID or (2) the resulting liquid NSAID composition did not yield a satisfactory dispersion of NSAID active agent upon contact with gastric juice. Acacia formed a precipitate in the liquid composition. Alginic acid was not satisfactory. Sodium carboxymethylcellulose formed a flocculant after dilution, not a fine dispersion of active NSAID ingredient. "Carbopol 934", "Tandem 552", "PEG 200", "Tween 80" and "Span 80" also were not workable.

What is claimed is:

1. A one phase liquid composition for oral administration comprising:
   (a) An anti-inflammatory but non-toxic quantity of a non-steroidal, anti-inflammatory drug in carboxylic acid form or a non-toxic, pharmaceutically acceptable alkali metal or ammonium salt thereof;
   (b) a pharmaceutically acceptable quantity of a glycol which is propylene glycol or a polyethylene glycol selected from the range of 15–50% v/v;
   (c) a quantity of ethanol selected from the range of 0–20% v/v;
   (d) a pharmaceutically acceptable quantity of a polyol which is glycerin or sorbitol selected from the range of 30–80% v/v; and
   (e) a pharmaceutically acceptable quantity of a dispersing agent which is polyvinylpyrrolidone, hydroxypropylcellulose or hydroxypropylmethylcellulose and which is selected form the range of 50:1 to 1:3 w/w of drug: dispersing agent.

2. The composition of claim 1 in which the dispersing agent is polyvinylpyrrolidone K 28–32.

3. The composition of claim 1 in which the drug is selected from the group consisting of diclofenac, fenoprofen, flurbiprofen, ibuprofen, indomethacin, ketoprofen, naproxen, etodolac and sulindac.

4. The composition of claim 1 in which the drug is sulindac.

5. The composition of claim 1 in which the drug is calcium diclofenac.

6. The composition of claim 3 in which the glycol is propylene glycol, the polyol is sorbitol and the disbursing agent is polyvinylpyrrolidone K 28-32(.) the latter being present in the ratio of drug:dispersing agent of 1:1 by weight.

7. The composition of claim 1 in which the drug is in the form of the calcium salt.

8. The composition of claim 1 in which the drug is calcium sulindac.

9. The composition of claim 1 in which the drug is tromethamine ketoprofen.

10. The composition of claim 1 in which the drug is a calcium, sodium, potassium or tromethane salt.

11. The composition of claim 3 in which the drug is a calcium, sodium, potassium or tromethane salt.

12. A method of treating a human subject in need of anti-inflammatory or analgesic treatment comprising orally administration to said subject a composition of claim 1.

* * * * *